United States Patent
Tamiya et al.

(10) Patent No.: US 8,664,003 B2
(45) Date of Patent: Mar. 4, 2014

(54) CHIP PROVIDED WITH FILM HAVING HOLE PATTERN WITH THE USE OF THERMORESPONSIVE POLYMER AND METHOD OF PRODUCING THE SAME

(75) Inventors: Eiichi Tamiya, Toyonaka (JP); Yoshiyuki Yokoyama, Toyama (JP); Satoshi Fujiki, Toyama (JP); Katsumi Tanino, Takaoka (JP); Atsushi Muraguchi, Toyama (JP); Hiroyuki Kishi, Toyama (JP); Yoshiharu Tokimitsu, Toyama (JP); Shohei Yamamura, Takamatsu (JP)

(73) Assignees: Toyama Prefecture, Toyama (JP); Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/569,291

(22) Filed: Aug. 8, 2012

(65) Prior Publication Data

US 2012/0301942 A1    Nov. 29, 2012

Related U.S. Application Data

(62) Division of application No. 11/992,594, filed as application No. PCT/JP2006/319163 on Sep. 27, 2006, now abandoned.

(30) Foreign Application Priority Data

Sep. 30, 2005  (JP) ................................. 2005-287634

(51) Int. Cl.
  *C12Q 1/24*  (2006.01)
(52) U.S. Cl.
  USPC ........................... 436/177; 436/174; 422/68.1
(58) Field of Classification Search
  USPC ........................ 436/164, 172, 178, 174, 177; 435/287.2, 7.1, 287.1, 287.9, 288.7, 435/6.11, 6.16, 288.4, 4; 422/68.1, 82.05, 422/82.08
  See application file for complete search history.

(56) References Cited

U.S. PATENT DOCUMENTS

2002/0001813 A1   1/2002   Taylor et al.
(Continued)

FOREIGN PATENT DOCUMENTS

| JP | A-09-023876 | 1/1997 |
|---|---|---|
| JP | A-2003-102466 | 4/2003 |

(Continued)

OTHER PUBLICATIONS

Bio Industry, vol. 20, No. 7, pp. 60-67 (2003). (with abstract).

(Continued)

*Primary Examiner* — Christopher A Hixson
(74) *Attorney, Agent, or Firm* — Oliff PLC

(57) ABSTRACT

A chip useful for treating cells and the like which has a mechanism and a structure wherein the size of a hole pattern is arbitrarily changed so that cells can easily move in and get out from the hole in scattering or collecting cells but can hardly get out from the hole during washing or antigen-stimulation. The chip comprises a crosslinked product of a temperature-responsive polymer as a constituting member and being provided with a film having a hole pattern on the surface of a baseboard. A method of producing the chip comprises applying a composition containing a crosslinkable temperature-responsive polymer on the surface of a baseboard to thereby form a coating film, crosslinking the coating film to thereby form the crosslinked product as described above and then forming a hole pattern on the coating film of the crosslinked product.

15 Claims, 4 Drawing Sheets

(56) References Cited

U.S. PATENT DOCUMENTS

| | | |
|---|---|---|
| 2004/0175710 A1 | 9/2004 | Haushalter |
| 2004/0191891 A1 | 9/2004 | Tsinberg et al. |
| 2006/0134704 A1 | 6/2006 | Muraguchi et al. |
| 2007/0231363 A1 | 10/2007 | Chen et al. |
| 2008/0057561 A1 | 3/2008 | Takahashi et al. |

FOREIGN PATENT DOCUMENTS

| | | |
|---|---|---|
| JP | A-2004-173681 | 6/2004 |
| WO | WO 00/08472 | 2/2000 |
| WO | WO 2004/073843 A1 | 9/2004 |
| WO | WO 2005/095510 A1 | 10/2005 |

OTHER PUBLICATIONS

Yoshiyuki Yokoyama et al., "Seitai Zairyo no Bisai Pattern Keisei to sono Oyo ni Kansuru Knkyu", *Reports of the Toyama Industrial Technology Center*, No. 19, pp. IV-85-IV-86, Jul. 2005.

Xue et al., "Rapid Swelling and Deswelling in Cryogels of Crosslinked poly(N-isopropylacrylamide-co-acrylic acid)," European Polymer Journal 40 (2004), pp. 467-476.

Sayll et al., "Macroporous poly(N-isopropyl)acrylamide Formation Conditions," Polymer 42 (2001); pp. 7639-7652.

Cicek et al., "Preparation and Characterization of Thermoresponsive Isopropylacrylamide-Hydroxyethylmethacrylate Copolymer Gels," Journal of Polymer Science: Part A: Polymer Chemistry 46 (1998), pp. 527-541.

Nov. 14, 2006 International Search Report issued in PCT/JP2006/319163.

AFTER DROPPING LYMPHOCYTE SUSPENSION

AFTER WASHING / LIBERATING

CHIP PROVIDED WITH FILM HAVING HOLE PATTERN WITH THE USE OF THERMORESPONSIVE POLYMER AND METHOD OF PRODUCING THE SAME

This is a Division of application Ser. No. 11/992,594 filed Jul. 3, 2008, which in turn is a National Phase of Application No. PCT/JP2006/319163 filed Sep. 27, 2006. The disclosure of the prior applications is hereby incorporated by reference herein in its entirety.

TECHNICAL FIELD

The present invention relates to a chip being provided with a film having a hole pattern with the use of a thermoresponsive polymer on the surface of a substrate substrate and a method of producing the same.

BACKGROUND ART

A poly(N-isopropylacrylamide) (PNIPAAm) is known as a thermoresponsive polymer. An aqueous solution of PNIPAAm causes a phase separation due to a change in the temperature and at 31° C. or lower, it is dissolved in water and at a higher temperature, it is insolubilized and is separated out. N-isopropylacrylamide (NIPAAm) is easily polymerized with a radical initiator to obtain a PNIPAAm. Further, NIPAAm is known to be copolymerized with other functional monomers and the thus obtained polymer responds to various stimulation such as not only a change in the temperature, but also a light, an electric field, a change in pH and a solvent exchange.

A thermoresponsive polymer is known also to be used as a material for immobilizing biological materials (Japanese Patent Application Publication No. JP-A-2003-102466 (Patent Document 1) and Japanese Patent Application Publication No. JP-A-Hei 9-23876 (Patent Document 2)).

On the other hand, it has been attempted that an individual cell is specified, discriminated and a discriminated individual cell is used. For example, a study is made on that an antigen specificity of an individual lymphocyte is individually detected; a detected individual antigen-specific lymphocyte is collected; and using the collected individual antigen-specific lymphocyte, for example an antibody is produced (Tamiya et. al., "BIO INDUSTRY" Vol. 20, No. 7 (2003), pp. 60-67 (Non-Patent Document 1), Japanese Patent Application Publication No. JP-A-2004-173681 (Patent Document 3)).

However, an usual coated film of PNIPAAm is extremely easily dissolved in water or a polar organic solvent. Accordingly, when using a coated film of PNIPAAm, a biological material such as a cell is attempted to be immobilized, a part thereof which has been contacted with water is dissolved out on and on. Further, when for fine-processing a coated film of PNIPAAm, a resist is overcoated on an upper layer of the coated film of PNIPAAm, PNIPAAm is dissolved into a solvent of the resist, so that the both layers are mixed.

Thus, the present inventors not only have provided a material (NIPAAm) which is insoluble in water, an aqueous solution, and an organic solvent and has thermoresponsivity, but also have developed a chip utilizing a change in an adhering force to a cell which is caused by such a nature of a thermoresponsive material that the property of the material is changed from hydrophilic to hydrophobic corresponding to the change in the temperature, and have applied the patent (WO 2005/095510).

However, with respect to a chip utilizing a temperature-responsibility by which a material is changed from hydrophilic to hydrophobic (as a result, the adhering force to the cell is changed), there has been found such a drawback that when in a washing process, the cell is washed too strongly, all lymphocytes are washed away, on the contrary, when the cell is washed too weakly, lymphocytes are remained at a position where lymphocytes need not to be remained.

Thus, the object of the present invention is to provide a novel chip useful for treating cells and the like which has a mechanism and a structure wherein the size of a hole pattern is arbitrarily changed so that cells can easily move in and get out from the hole during scattering or collecting cells but can hardly get out from the hole during washing or antigen-stimulation.

DISCLOSURE OF THE INVENTION

Means for Solving the Problems

The present invention for solving the above problems is as follows.

[1] A chip includes a crosslinked product of a temperature-responsive polymer as a constituting member and is provided with a film having a hole pattern on the surface of a substrate.

[2] In the chip according to [1], the crosslinked product of the temperature-responsive polymer is either a crosslinked product between the temperature-responsive polymers or a crosslinked product through a crosslinker.

[3] In the chip according to [1] or [2], the crosslinked product of the temperature-responsive polymer is a crosslinked product of an N-alkyl (meth)acrylamide copolymer having a recurring unit represented by general formula (1):

[Chemical Formula 1]

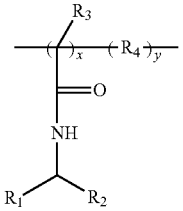

(1)

wherein $R_1$ and $R_2$ may be the same as or different from each other and represent a hydrogen atom or an (1-4C) alkyl group; $R_3$ represents a hydrogen atom or a methyl group; $R_4$ represents a hydrocarbon structure having a functional group crosslinkable with the above crosslinker; x and y are any numbers satisfying numerical formulae: $x+y=1$, $0<x\leq1$, and $0\leq y<1$, and having a weight average molecular weight of 500 to 5,000,000, with a crosslinker

[4] In the chip according to any one of [1] to [3], the film having a hole pattern has a thickness ranging from 10 nm to 1000 μm.

[5] In the chip according to any one of [1] to [4], the hole of the hole pattern has such a size that an inscribed circle thereof has a diameter ranging from 10 nm to 1000 μm.

[6] In the chip according to any one of [1] to [5], the hole of the hole pattern has a depth ranging from 10 nm to 100 μm.

[7] In the chip according to any one of [1] to [6], the hole of the hole pattern is provided in a density of 1 to 1,000,000,000 pieces/cm².

[8] In the chip according to any one of [1] to [7], the substrate has concave portions below at least a part of the holes which the film has on the surface of the substrate on which the film is provided.

[9] In the chip according to any one of [1] to [8], the hole of the hole pattern has on the surface of the substrate therein, a dot formed with the crosslinked product of the temperature-responsive polymer which is independent from the film.

[10] The chip according to any one of [1] to [9], the size of the hole of the hole pattern is changed arbitrarily by changing a part of or the whole of the film temperature to swell or contract a part of or the whole of the film.

[11] In the chip according to [10], a biological material housed in the hole of the hole pattern is caused to be either in a clathrated state or in a liberated state depending on the change in the film temperature.

[12] A method for clathrating a biological material in the hole pattern of the chip includes:
controlling the film temperature of the chip according to any one of [1] to [9] to a temperature at which the diameter of the hole of the hole pattern which the chip has become a size capable of housing the biological material;
housing the biological material in the hole of the hole pattern; and
controlling the film temperature of the chip to a temperature at which the diameter of the hole having housed the biological material becomes a size capable of clathrating the biological material.

[13] A method for liberating the biological material clathrated in the chip includes:
controlling the film temperature of the chip having clathrated the biological material by the method according to [12] to a temperature at which the diameter of the hole of the hole pattern of the chip becomes a size capable of liberating the biological material.

[14] A production method of a chip which includes a crosslinked product of a temperature-responsive polymer as a constituting member and is provided with a film having a hole pattern on the surface of the substrate, is characterized by including:
forming a coated film by applying to the surface of the substrate, a composition containing a crosslinkable temperature-responsive polymer, a composition containing a crosslinkable temperature-responsive polymer and a crosslinker, or a composition containing a temperature-responsive polymer and a crosslinker;
crosslinking the coated film to form the crosslinked product; and
forming the hole pattern on the coated film of the crosslinked product.

[15] In the production method according to [14], the composition containing the crosslinkable temperature-responsive polymer and a crosslinker or the composition containing a temperature-responsive polymer and a crosslinker is a composition containing an N-alkyl (meth)acrylamide copolymer having a recurring unit represented by general formula (1):

[Chemical Formula 2]

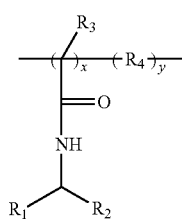

(1)

wherein $R_1$ and $R_2$ may be the same as or different from each other and represent a hydrogen atom or an (1-4C) alkyl group; $R_3$ represents a hydrogen atom or a methyl group; $R_4$ represents a hydrocarbon structure having a functional group crosslinkable with the above crosslinker; x and y are any numbers satisfying numerical formulae: $x+y=1$, $0<x\leq1$, and $0\leq y<1$; and here, (meth)acrylamide represents both methacrylamide and acrylamide,
and having a weight average molecular weight of 500 to 5,000,000, and a crosslinker.

[16] A production method of a chip which includes a crosslinked product of a temperature-responsive polymer as a constituting member and is provided with a film having a hole pattern on the surface of a substrate, is characterized by including:
forming a coated film by applying to the surface of the substrate, a composition containing a monomer for forming a crosslinkable temperature-responsive polymer, a composition containing a monomer for forming a crosslinkable temperature-responsive polymer and a crosslinker, or a composition containing a monomer for forming a temperature-responsive polymer and a crosslinker;
polymerizing and crosslinking the coated film to form the crosslinked product; and
forming the hole pattern on the coated film of the crosslinked product.

[17] In the production method according to any one of [14] to [16], the substrate to which the composition is applied is a silicon substrate, a glass substrate, a plastic substrate, a mica substrate, a ceramic substrate or a metal substrate.

[18] The production method according to any one of [14] to [17], is characterized in that the application of the composition to the substrate includes:
dissolving the composition in a solvent;
dropping the resultant solution onto the substrate; and
evaporating the solvent to obtain a coated film.

[19] In the production method according to any one of [14] to [18], the formation of the hole pattern on the coated film is performed by a photolithography method.

[20] In the production method according to [19], the formation of the hole pattern on the coated film by a photolithography method includes:
incorporating further an acid generator in the composition for forming the coated film;
irradiating, after forming the coated film, a radiation for activating the acid generator through a mask for forming the hole pattern to the coated film;
crosslinking a part of the coated film to which a radiation has been irradiated; and
removing, after removing the mask, a part of the coated film which has not been crosslinked.

[21] In the production method according to [20], the acid generator is at least one selected from the group consisting of an onium salt, sulfonyloxyimide, triazine and a sulfonate ester.

[22] In the production method according to [20] or [21], the radiation is a mercury lamp light, an electron beam, an excimer laser, an X ray or a xenon lamp.

[23] In the production method according to any one of [14] to [18], the forming of the hole pattern on the coated film is performed by a screen printing method, an inkjet method, a contact printing method or an emboss processing method.

[24] In the production method according to [23], the forming of the hole pattern on the coated film by a screen printing method, an inkjet method, a contact printing method or an emboss processing method is performed by forming the hole pattern on the coated film before the crosslinking and then by crosslinking the coated film on which the hole pattern has been formed.

[25] In the production method according to any one of [15] to [24], the hydrocarbon structure having a functional group crosslinkable with the crosslinker is a (meth)acrylate structure or a (meth)acrylamide structure (here, the (meth)acrylate represents both methacrylate and acrylate) having in a side chain thereof, a functional group crosslinkable with the crosslinker.

[26] In the production method according to any one of [15] to [25], the functional group crosslinkable with the crosslinker is a hydroxyl group, a carboxyl group, an epoxy group, an amino group or a succinimide group.

[27] In the production method according to any one of [15] to [26], the crosslinker is an epoxy-based crosslinker, a melamine-based crosslinker, a glycouril-based crosslinker, or a compound having two or more of hydroxyl groups, carboxyl groups, azide groups, or vinylether groups.

[28] In the production method according to [26] or [27], the compound having two or more of hydroxyl groups, carboxyl groups, azide groups, or vinylether groups is 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene, 2,7-dihydroxynaphthalene, 1,3-cyclopentanediol, 2,6-quinolinediol, 2,3-dihydroxyquinoxaline, 1,4-dioxanediol, 1,4-cyclohexanedimethanol, polyvinyl alcohol, 1,2-naphthalene dicarboxylic acid, 1,3-naphthalene dicarboxylic acid, 1,4-naphthalene dicarboxylic acid, 1,5-naphthalene dicarboxylic acid, 1,6-naphthalene dicarboxylic acid, 1,7-naphthalene dicarboxylic acid, 1,8-naphthalene dicarboxylic acid, 2,3-naphthalene dicarboxylic acid, 2,6-naphthalene dicarboxylic acid, cyclohexane dicarboxylic acid, terephthalic acid, 1,2-cyclopentane dicarboxylic acid, 2,5-thiophene dicarboxylic acid, 2-methyl-3,4-quinoline dicarboxylic acid, 9,10-anthracene dicarboxylic acid, dihydroanthracene-9,10-dicarboxylic acid, citric acid, succinic acid, polyacrylic acid, polymethacrylic acid, 2,6-bis(4-azidebenzilidene)cyclohexanone, bis(4-vinyloxybutyl)terephthalate or bis(4-vinyloxybutyl)adipate.

Effects of the Invention

According to the present invention, using a material having thermoresponsivity, a novel chip for cells and the like which has a mechanism and a structure wherein cells can easily move in and get out from the hole during scattering or collecting cells but can hardly get out from the hole during washing or antigen-stimulation, can be provided.

BEST MODES FOR CARRYING OUT THE INVENTION (Temperature-Responsive Polymer Composition)

The chip of the present invention includes a crosslinked product of a temperature-responsive polymer as a constituting member and is provided with a film having a hole pattern on the surface of the substrate, and the method of producing the chip consists mainly of three steps of forming a coated film, crosslinking the coated film and forming a hole pattern.

The formation of the coated film is broadly classified into (1) a method of forming the coated film by applying to the surface of the substrate, a composition containing a crosslinkable temperature-responsive polymer, a composition containing a crosslinkable temperature-responsive polymer and a crosslinker, or a composition containing a temperature-responsive polymer and a crosslinker (a method according to claims 14) and (2) a method of forming the coated film by applying to the surface of the substrate, a composition containing a monomer for forming a crosslinkable temperature-responsive polymer, a composition containing a monomer for forming a crosslinkable temperature-responsive polymer and a crosslinker, or a composition containing a monomer for forming a temperature-responsive polymer and a crosslinker (a method according to claim 16). The method of (1) is a method using a temperature-responsive polymer and the method of (2) is a method using a monomer for forming a temperature-responsive polymer. In the method of (1), the composition containing a temperature-responsive polymer is prepared beforehand and a crosslinking reaction is performed after the formation of the coated film to obtain the film. On the contrary, in the method of (2), a composition containing a monomer for forming the temperature-responsive polymer is applied to the substrate and a polymerization reaction and a crosslinking reaction for obtaining a temperature-responsive polymer are performed to obtain the film. The method of (1) is more preferred in terms not only of capable of synthesizing, preparing a large amount of the composition in different vessels, but also of the easiness to form the coated film and of capable of forming fine holes.

First, the method of (1) is described.

In the method of (1), used is any one composition containing a temperature-responsive polymer among (a) a composition containing a crosslinkable temperature-responsive polymer, (b) a composition containing a crosslinkable temperature-responsive polymer and a crosslinker, and (c) a composition containing a temperature-responsive polymer and a crosslinker. In the composition (a), the temperature-responsive polymer is a crosslinkable polymer and the crosslinking after the formation of the coated film is performed using a crosslinkable group which the temperature-responsive polymer has. In this case, the polymer chains are directly crosslinked to each other. In the composition (b), not only the temperature-responsive polymer is a crosslinkable polymer, but also a crosslinker is contained, so that the crosslinking after the formation of the coated film is performed using both a crosslinkable group which the temperature-responsive polymer has and the crosslinker. In this case, a direct crosslink between the polymer chains and a crosslink through the chain of the crosslinker are formed. In the composition (c), the temperature-responsive polymer is a polymer having no crosslinkable group, but a crosslinker is contained, so that the crosslinking after the formation of the coated film is performed by the crosslinker. In this case, a crosslink through the chain of the crosslinker is formed.

The crosslink through the chain of a crosslinker which results in that the polymer chains are linked through a flexible chain of the crosslinker, is more preferred than a direct crosslink of the polymer chains to each other from the viewpoint of the temperature-responsibility (changed amount of volume during swelling and contracting, responding speed) after crosslinking.

The temperature-responsive polymer having a functional group reactable with a crosslinker may be a copolymer produced by copolymerizing a site expressing the temperature-responsibility with a site having a functional group readable with a crosslinker.

The temperature-responsive polymer crosslinkable between the crosslinkable groups may be a copolymer produced by copolymerizing a site expressing temperature-responsibility with a site having a crosslinkable group in a polymer chain which can be crosslinked with another crosslinkable group.

The temperature-responsive polymer having no crosslinkable group may be a homopolymer including only a site expressing temperature-responsibility or a copolymer with another monomer. As a usable crosslinker, there can be mentioned a crosslinker having two or more radical generating groups. A radical generating group contained in a crosslinker can link the crosslinker itself to any part of a covalent bond constituting a temperature-responsive polymer by high reactivity thereof. As the radical generating group, there can be mentioned an azide group and as the crosslinker, there can be mentioned 2,6-bis(azidebenzilidene)cyclohexanone, 4,4'-diazidestilben-2,2'-disulfonic acid disodium.

The copolymer of a site expressing temperature-responsibility with a site having a functional group reactable with a crosslinker may be an N-alkyl (meth)acrylamide copolymer having a recurring unit represented by general formula (1) and having a weight average molecular weight of 500 to 5,000,000. The N-alkyl (meth)acrylamide copolymer has preferably a weight average molecular weight ranging from 5,000 to 100,000 from the viewpoint of the viscosity of a coating solution containing the copolymer and the swelling performance of the copolymer after crosslinked.

[Chemical Formula 2]

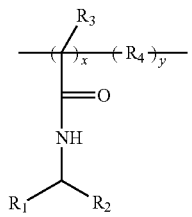

(1)

In general formula (1), $R_1$ and $R_2$ may be the same as or different from each other and represent a hydrogen atom or an (1-4C) alkyl group of which examples include a methyl group, an ethyl group, a propyl group and a butyl group; $R_3$ represents a hydrogen atom or a methyl group; $R_4$ represents a hydrocarbon structure having a functional group crosslinkable with the above crosslinker; x and y are any numbers satisfying numerical formulae: x+y=1, $0<x\leq1$ and $0\leq y<1$, preferably satisfying numerical formulae: $0.6<x\leq0.95$ and $0.05\leq y<0.4$; an x component is a chemical structure taking charge of temperature-responsibility and a y component is a chemical structure taking charge of the crosslinking reaction; when x is in a range of $0.6<x$, temperature-responsibility can be thoroughly maintained, which is preferred, and when y is in a range of $0.05\leq y$, thorough crosslinking density (solvent resistance) can be obtained, which is preferred; further from the viewpoint of a range in which temperature-responsibility can be maintained and thorough crosslinking density can be obtained, ranges of $0.6<x\leq0.95$ and $0.05\leq y<0.4$ are preferred; and here, (meth)acrylamide represents both methacrylamide and acrylamide.

The structure of the site expressing temperature-responsibility is not particularly limited, however is preferably an N-alkyl (meth)acrylamide structure contained in general formula (1), more preferably an N-isopropyl acrylamide structure, from the viewpoint of temperature-responsibility performance (changed amount of volume during swelling and contracting, responding speed). Further, in such terms that since the copolymerization with other functional monomers is easy, the resultant copolymer can be varied to respond to various stimulations such as a light, an electrical field, a change in pH, a solvent exchange and an antigen-antibody recognition, the N-alkyl (meth)acrylamide structure is preferred.

Specific examples of the structure of the site expressing temperature-responsibility include N-isopropyl (meth)acrylamide, N-ethyl (meth)acrylamide, N-n-propyl (meth)acrylamide, N-cyclopropyl (meth)acrylamide, N,N-diethyl (meth)acrylamide, N-acryloylpiperidine, N-acryloylpyrrolidine, N-vinyl isobutylamide, 2-carboxylsopropyl (meth)acrylamide, (meth)acrylamide having polyethyleneoxide in a side chain thereof, and (meth)acrylate having polyethyleneoxide in a side chain thereof. Since the temperature-responsive polymers using the above structures have an inherent phase transition temperature (lower critical temperature; LCST), a structure thereof to be used can be selected corresponding to a desired transition temperature.

The structure of the site having a functional group reactable with a crosslinker may be a (meth)acrylate structure or (meth)acrylamide structure having in a side chain thereof, a reactive group reactable with a crosslinker (carboxyl group, epoxy group, amino group, succinimide group and the like). Specific examples of such a structure include hydroxyethyl (meth)acrylate, hydroxyethyl (meth)acrylamide, (meth)acrylic acid, glycidyl (meth)acrylate, glycidyl (meth)acrylamide, (meth)acrylic acid succinimide ester, γ-hydroxyl acid (meth)acrylate, γ-hydroxyl acid (meth)acrylamide, and 2-carboxylsopropyl (meth)acrylamide. The molar fraction of the site having a functional group reactable with a crosslinker in the polymer can be appropriately determined taking into consideration the crosslinking density and degree of swelling of the polymer film and can be, for example in a range of 1 to 50 mol %.

As the temperature-responsive polymer having a functional group reactable with a crosslinker, a temperature-responsive polymer having inherently in the chemical structure thereof, a reactive group reactable with a crosslinker (hydroxyl group, carboxyl group, amino group, epoxy group and the like) can be used as a homopolymer as it is without copolymerizing. Examples of such a temperature-responsive polymer include polyhydroxypropyl acrylate, polyvinyl alcohol, methyl cellulose, hydroxypropyl methylcellulose, hydroxypropyl cellulose, 2-carboxyisopropyl (meth)acrylamide, soluble elastin protein, Poly(VPGVG) (wherein V represents valine; P represents proline; and G represents glycine) which is a polypeptide, and a polyethylene oxide having a hydroxyl group at the terminal thereof. Since the above temperature-responsive polymers have an inherent phase transition temperature (lower critical temperature; LCST), the polymer to be used can be selected corresponding to a desired transition temperature. Further, elastin, Poly(VPGVG) and cellulose-based polymer as a temperature-responsive polymer derived from the living body are preferred in terms of biocompatibility when they are used as a biochip.

The crosslinker can be, for example an epoxy-based crosslinker, a melamine-based crosslinker, a glycouril-based crosslinker, or a compound having two or more of hydroxyl groups, carboxyl groups, azide groups, or vinylether groups.

The epoxy-based crosslinker can be, for example trimethylolpropanetriglycidylether, 1,2-cyclohexane dicarboxylic acid diglycidyl ester, 1,2-naphthalene dicarboxylic acid diglycidyl ester, 1,3-naphthalene dicarboxylic acid diglycidyl ester, 1,4-naphthalene dicarboxylic acid diglycidyl ester, 1,5-naphthalene dicarboxylic acid diglycidyl ester, 1,6-naphthalene dicarboxylic acid diglycidyl ester, 1,7-naphthalene dicarboxylic acid diglycidyl ester, 1,8-naphthalene dicarboxylic acid diglycidyl ester, 2,3-naphthalene dicarboxylic acid diglycidyl ester, 2,6-naphthalene dicarboxylic acid diglycidyl ester, 2,7-naphthalene dicarboxylic acid diglycidyl ester, 1,4-cyclohexane dimethanol diglycidyl ether, bisphenol-A-diglycidyl ether, bisphenol-5-diglycidyl ether, bis(4-(2,3-epoxypropylthio)phenyl)sulfide, or 1,4-bis(glycidyloxy)benzene.

The melamine-based crosslinker can be, for example hexamethoxymethylmelamine, hexaethoxymethylmelamine or hexapropoxymethylmelamine The glycouril-based crosslinker can be, for example 1,3,4,6-tetrakis(methoxymethyl)glycouril, 1,3,4,6-tetrakis(ethoxymethyl)glycouril, or 1,3,4,6-tetrakis(propoxymethyl)glycouril.

The compound having two or more of hydroxyl groups, carboxyl groups, azide groups, or vinylether groups can be, for example 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene, 2,7-dihydroxynaphthalene, 1,3-cyclopentanediol, 2,6-qinolinediol, 2,3-dihydroxyquinoxaline, 1,4-dioxanediol, 1,4-cyclohexanedimethanol, polyvinylalcohol, 1,2-naphthalene dicarboxylic acid, 1,3-naphthalene dicarboxylic acid, 1,4-naphthalene dicarboxylic acid, 1,5-naphthalene dicarboxylic acid, 1,6-naphthalene dicarboxylic acid, 1,7-naphthalene dicarboxylic acid, 1,8-naphthalene dicarboxylic acid, 2,3-naphthalene dicarboxylic acid, 2,6-naphthalene dicarboxylic acid, cyclohexane dicarboxylic acid, terephthalic acid, 1,2-cyclopentane dicarboxylic acid, 2,5-thiophene dicarboxylic acid, 2-methyl-3,4-quinoline dicarboxylic acid, 9,10-anthracene dicarboxylic acid, dihydroanthracene-9,10-dicarboxylic acid, citric acid, succinic acid, polyacrylic acid, polymethacrylic acid, 2,6-bis(4-azidebenzylidene)cyclohexanone, bis(4-vinyloxybutyl)terephthalate or bis(4-vinyloxybutyl)adipate.

The content of the crosslinker can be appropriately determined taking into consideration, the crosslinking density and degree of swelling of the temperature-responsive polymer film, and can be, for example in a range of 0.5 to 50 parts by weight relative to 100 parts by weight of the temperature-responsive polymer. A crosslinker transparent and nonluminescent relative to a light having a wavelength of 400 nm to 600 nm is more preferred than an opaque or luminescent crosslinker, because such a crosslinker does not hinder an observation by an optical microscope and a fluorescence observation. Further, when a water-soluble crosslinker is used, water can be used as a solvent for the coating liquid, which is more preferred than in the case of using an organic solvent from the viewpoint of the environmental burden and which is also preferred in terms of capable of applying the coating liquid even to a substrate having low solvent resistance.

As described above, the method of (1) "a method of using a composition containing a temperature-responsive polymer" is described. A monomer for forming a temperature-responsive polymer used in the method (2) "a method of using a composition containing a monomer for forming a temperature-responsive polymer" can be a monomer containing each structure as described above where the monomer is described as a constituting member of the above polymer.

Examples of the monomer containing a site expressing temperature-responsibility include N-isopropyl (meth)acrylamide monomer, N-ethyl (meth)acrylamide monomer, N-n-propyl (meth)acrylamide monomer, N-cyclopropyl (meth)acrylamide monomer, N,N-diethyl (meth)acrylamide monomer, N-acryloyl piperidine monomer, N-acryloyl pyrrolidine monomer, N-vinylisobutylamide monomer, 2-carboxylsopropyl (meth)acrylamide monomer, (meth)acrylamide monomer having polyethyleneoxide in a side chain thereof and (meth)acrylate monomer having polyethyleneoxide in a side chain thereof.

Examples of the monomer containing a site having a functional group reactable with a crosslinker include hydroxyethyl (meth)acrylate monomer, hydroxyethyl (meth)acrylamide, (meth)acrylic acid monomer, glycidyl (meth)acrylate monomer, glycidyl (meth)acrylamide monomer, (meth)acrylic acid succinimide ester monomer, γ-hydroxyl acid (meth)acrylate monomer, γ-hydroxyl acid (meth)acrylamide monomer, and 2-carboxylsopropyl (meth)acrylamide monomer.

The crosslinker used in the method (2) is the same as that mentioned in the method (1). Further, a compound having two or more polymerizable groups can be used as a crosslinker. Specific examples thereof include bis(meth)acrylamide monomer and bis(meth)acrylate monomer. Further, the content of the crosslinker can be appropriately determined based on the description with respect to the polymers in (1).

(Formation of Coated Film)

The formation of the coated film is performed in the method (1) by dissolving a composition containing any one temperature-responsive polymer among the above (a) to (c) in a solvent and by applying the resultant solution to a substrate, and in the method (2) by dissolving a composition containing a corresponding monomer in a solvent and by applying the resultant solution to a substrate, with proviso that there is a case where the coated film can be formed without using a solvent. In such a case, the coated film may be formed without using a solvent.

Examples of the solvent in which the composition is dissolved for preparing a coating liquid of the composition include water, methanol, ethanol, 1-methoxy-2-propanol, ethylene glycol monomethyl ether, methyl cellosolve acetate, toluene, xylene, diacetone alcohol, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactate and butyl lactate. These solvents can be used individually or in combination of two or more thereof. The amount of the solvent can be appropriately determined taking into consideration a desired solution viscosity and the thickness of the resultant coated film, and can be, for example in a range of 100 to 5000 parts by weight relative to 100 parts by weight of the temperature-responsive polymer. Particularly, when the crosslinker is water-soluble and water is used as a solvent for the coating liquid, it is more preferred than in the case of using an organic solvent from the viewpoint of the environmental burden and it is also preferred in terms of capable of applying the coating liquid even to a substrate having low solvent resistance.

The substrate on which a coated film is fainted can be, for example a silicon substrate, a glass substrate, a plastic substrate, a mica substrate, a ceramics substrate or a metal substrate.

For fixing firmly the substrate and the temperature-responsive polymer film to each other by the crosslinking reaction, when the substrate is a glass substrate, a silicon wafer or a quartz substrate, it is preferred to use as a surface treating agent, a silane coupling agent having a hydroxyl group, a carboxyl group, an epoxy group or an amino group at a molecule terminal thereof. In the case of a gold substrate, it is preferred to use a thiol compound having a hydroxyl group, a carboxyl group, an epoxy group or an amino group at a molecule terminal thereof. In the case of a mica substrate or a plastic substrate, it is preferred to subject the substrate surface to a treatment for forming a hydroxyl group or carboxyl group on the substrate surface by performing an oxygen plasma treatment, an UV treatment or an ozone treatment instead of using a surface treating agent.

(Crosslinking and Hole Pattern Forming)

With respect to crosslinking (polymerizing and crosslinking a monomer in the case (2)) the coated film formed on the substrate and forming the hole pattern on the coated film, the procedure thereof is partially varied depending on the method of forming the hole pattern.

The forming of the hole pattern can be performed, for example by a photolithography method, an emboss processing method, a screen printing method, a contact printing method or an inkjet method.

In the photolithography method, the hole pattern forming is performed after the formation of the coated film by performing the photolithography through a mask. It is performed also by inkjet-printing or by screen-printing through a mask. Besides them, the hole pattern forming is performed by a contact printing method including: applying the above coating solution to a convex part of a stamper having convexity and concavity; and butting the stamper to a substrate to transcribe the solution, or by an emboss processing method comprising: forming a coated film on a substrate; and butting a stamper having convexity and concavity to the substrate to transcribe a convexoconcave pattern. Further, the hole formed by the above process may penetrate the coated film fully or not fully.

Hole Pattern Forming Process Using Photolithography Method

Hereinafter, a photolithography method using an acid generator is described. In this method, the coated film forming is performed by applying a solution in which the above composition containing thermoresponsive polymer or composition containing a monomer for forming a thermoresponsive polymer and an acid generator are dissolved in a solvent, to the substrate, and the hole pattern is formed by a method including: irradiating a radiation for activating an acid generator to the resultant coated film through a mask; progressing a crosslinking reaction at a site where an acid catalyst has been generated by heating; and dissolving and removing an uncrosslinked site by the development.

The acid generator may be any one agent so long as it generates an acid by irradiating an activated radiation and the activated radiation can be, for example a mercury lamp light, an electron beam, an excimer laser, an X ray or a xenon lamp.

The acid generator may be any one agent so long as it generates an acid by irradiating an activated radiation and examples thereof include triphenylsulfonium triflate, triphenylsulfonium nonaflate, phenyldimethylsulfonium triflate, trimethylsulfonium triflate, dihydronaphthyldimethylsulfonium triflate, diphenyliodonium triflate, an onium salt such as triphenylsulfonium camphor sulfonic acid salt, sulfonyloxyimide such as N-trifluoromethanesulfonyloxynaphthylimide and N-methanesulfonyloxynaphthylimide, 2,4,6-tris(trichloromethyl)-1,3,5-triazine and sulfonic acid ester. An acid generator which is transparent and nonluminescent relative to a light having a wavelength of 400 nm to 600 nm is more preferred than an opaque or luminescent acid generator, because such an acid generator does not hinder an observation by an optical microscope and a fluorescence observation. Further, when a water-soluble acid generator is used, water can be used as a solvent for the coating liquid, which is more preferred than in the case of using an organic solvent from the viewpoint of the environmental burden and which is also preferred in terms of capable of applying the coating liquid even to a substrate having low solvent resistance. The content of the acid generator can be appropriately determined taking into consideration an exposure sensitivity required for the pattern forming and can be, for example in a range of 0.1 part by weight to 20 parts by weight relative to 100 parts by weight of the thermoresponsive polymer.

As the solvent for dissolving the composition and an acid generator, the same solvent as that described in the above section of forming the coated film can be used. Particularly, when both a water soluble crosslinker and a water soluble acid generator are used and as the solvent, water is used, it is more preferred than the case where an organic solvent is used from the viewpoint of the environmental burden. It is also preferred in terms of capable of applying to a substrate having low solvent resistance.

The developing liquid used for the development is not particularly limited so long as it can dissolve a temperature-responsive polymer in a uncrosslinked portion. Examples of the developing liquid include water, methanol, ethanol, 1-methoxy-2-propanol, ethyleneglycol monomethyl ether, methylcellosolve acetate, toluene, xylene, diacetone alcohol, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactate, butyl lactate and a tetramethylammonium hydroxide aqueous solution, each having a temperature of LCST or lower. These solvents can be used individually or in combination of two or more thereof. The developing time may be in a range of 10 seconds to 30 minutes.

The formation of the coated film is performed by applying the solution in which the above thermoresponsive polymer composition and an acid generator are dissolved in a solvent, to a substrate. By rotating the substrate to which the solution has been dropped, the solvent is evaporated to obtain the coated film. The evaporation of the solvent by rotating the substrate can be performed, for example by an air stream generated by the rotation, or further by heating from the outside using a heater.

The rotating speed of a spin coater can be appropriately determined taking into consideration a desired thickness of the coated film and may be in a range of, for example 500 to 8000 rpm. Further, since the here-obtained thickness of the coated film becomes the depth of the hole of the hole pattern of a temperature-responsive polymer obtained by a photolithography, by controlling the coated film thickness, a chip having any depth of the hole of the hole pattern can be produced.

Using water as a developing liquid is more preferred than using an organic solvent from the viewpoint of the environmental burden. It is also preferred in terms of capable of applying to a substrate having low solvent resistance. Further, it is also preferred for improving resolving properties. Usually, after the development, a developing liquid penetrates also into a crosslinked insolubilized portion and the portion is in a swelling state. When in such a state, the developing liquid is removed, the pattern form is disintegrated or the patterns are fused to each other, so that high resolving properties cannot be obtained. However, in the case where water is used during the development, at the time when water is removed after the development, when the temperature of water is temporarily raised to LCST or higher, water is expelled out of the inside of the swelling pattern and the pattern is contracted and hardened. Accordingly, the disintegration of the pattern can be prevented and high resolving properties can be obtained.

Hole Pattern Forming Process Using Screen Printing Method, Inkjet Method, Contact Printing Method or Emboss Processing Method Hereinafter, the hole pattern forming process using a screen printing method, an inkjet method, a contact printing method or an emboss processing method is described. In this method, the formation of the coated film is performed by applying the solution in which the above thermoresponsive polymer composition is dissolved in a solvent, to a substrate, by forming the hole pattern and then by progressing the crosslinking reaction of the coated film.

In the screen printing method, the above solution is screen-printed on a substrate through a mask to form a coated film having a hole pattern. In the inkjet method, the solution is injected to another part than the hole pattern to form a coated film having a hole pattern. In the contact printing method, by applying the above coating solution to a convex part of a stamper having convexity and concavity and by butting the stamper to a substrate to transcribe the solution to thereby form a coated film having a hole pattern. In the emboss processing method, by spin-coating the above solution on a substrate to form a coated film and thereafter, a stamper having convexity and concavity is butted to the substrate to transcribe a convexoconcave pattern to thereby form a coated film having a hole pattern.

A crosslinking by heating the coated film having a hole pattern can be performed, for example using a hot plate or a baking oven at a temperature ranging from 170° C. or more to 300° C. or less for 30 minutes or more and within 24 hours when the coated film contains no acid catalyst. Further, when the coated film contains an acid catalyst, the crosslinking by heating the coated film having a hole pattern can be performed using a hot plate or a baking oven at temperature ranging from 90° C. or more to less than 170° C. for 10 seconds or more and less than 30 minutes. Here, the acid catalyst may be an acid incorporated directly in the coating solution or an acid generated by irradiating a radiation to the coated film containing the above acid generator. Thus, the substrate having a coated film with a hole pattern, can be obtained.

When the monomer is used, a polymerization initiator is incorporated in the coating solution. By the polymerization initiator, the crosslinking reaction can be progressed simultaneously with the polymerization reaction. Examples of the polymerization initiator include azoisobutylonitrile, azoisobutylo butyric acid and benzoyl peroxide.

(Chip)

The chip of the present invention contains a crosslinked product of a temperature-responsive polymer as a constituting member, is provided with a film having a hole pattern on the surface of the substrate, and can be obtained by the above production method of the present invention. This chip is used, for example for clathrating or liberating a biological material in or out of a hole of the hole pattern by controlling the coated film temperature to open or close the size of the hole of the hole pattern. The thickness of the film having a hole pattern, the size of the hole, depth, figure, density, configuration (figure of the pattern) and the like can be appropriately determined corresponding to an object desired to be held on the substrate according to the purpose. The thickness of the film having a hole pattern may be, for example in a range of 10 nm to 100 µM. The figure of the hole of the hole pattern may be a circular form, a rectangular form (for example, square, rectangle, hexagonal shape), a pear-shaped form or a star-shaped form and the density of the hole may be, for example one to 1,000,000,000 pieces/cm$^2$. As the area of the hole, there can be mentioned 1 nm$^2$ or more and 1 cm$^2$ or less. As the size of the hole, the diameter of an inscribed circle of the hole may be in a range of 10 nm to 1000 µm and when the figure of the hole is a circular form, the diameter thereof may be, for example in a range of 10 nm to 1000 µm. These ranges are preferably in a range of 100 nm to 20 µm. The depth of the hole of the hole pattern is, for example in a range of 10 nm to 100 µm.

In the chip of the present invention, the substrate to which the composition is applied, can be a substrate having concave parts at the positions under at least a part of holes which the coated film will have, on the surface to which the composition is applied (FIG. 11). Alternatively, after the coated film has been applied to the substrate, at the positions of the substrate under at least a part of holes which the coated film has, concave parts can be formed later. In such a chip, the concave parts of the substrate are positioned under the holes of the coated film, and one hole of the coated film and one concave part of the substrate together form one well. Then, when the diameter of the hole is reduced due to a temperature change, a substance retained in a well can be retained in a concave part of the substrate. The cross sectional forms of the hole of the coated film and the concave part of the substrate may be the same as or different from each other. Further, the diameters of the hole of the coated film and the concave part of the substrate may be also the same as or different from each other. The depth of the concave part of the substrate can be appropriately determined corresponding to a substance to be retained and may be, for example in a range of 0.1 to 100 µm. Further, the bottom part of the concave part of the substrate may be in either a horizontal form, a hemisphere form or a rotating form (for example, a triangular pyramid form) relative to a center of the bottom part as the axis of the form and the like. Alternatively, the concave part of the substrate may have a through-hole admitting to the reverse surface of the substrate. The through-hole may have a plug or lid in an openable and closable manner and the cross section of the through-hole may be either smaller than, the same as or larger than that of the concave part of the substrate.

The chip of the present invention in which the concave part of the substrate is at the position below the hole of the above coated film and one hole of the coated film and one concave part of the substrate together form one well, can be formed as follows.

The solution in which the above thermoresponsive polymer composition and an acid generator are dissolved in a solvent, is applied to a planar substrate and the hole pattern is formed by the above photolithography. Next, utilizing the coated film in which the hole pattern has been formed as an etching mask, a part of the substrate exposed at a position below the hole is etched to a desired depth by a wet etching or a dry etching and the like. This method is more preferred than a method in which after the concave part has been formed in the substrate, the hole part of the coated film is formed aligning the hole part with the concave part, in terms of capable of performing the alignment easily and with high precision.

In the chip of the present invention, the hole of the hole pattern can have a dot formed independently from the coated film and using the above composition, on the surface of the substrate in the hole (FIG. 12). A crosslinked product for forming a coated film having a hole pattern may have the same composition as or a different composition from that of a crosslinked product for forming a dot. The chip of the present invention having a dot in the hole thereof can be formed as follows.

The solution in which the above thermoresponsive polymer composition and an acid generator are dissolved in a solvent, is applied to a planar substrate and the hole pattern is formed by the above photolithography. Next, to the coated film in which the hole pattern has been formed, the thermoresponsive polymer composition is injected at the position of the hole pattern by an inkjet method to form a dot inside the hole and thereafter, the dot is thermally crosslinked. In the chip having a dot on the surface of the substrate in the hole of the hole pattern, as shown in FIG. 10, not only the crosslinked product forming the coated film is expanded, so that the diameter of the hole is reduced, but also simultaneously a crosslinked product fanning the dot is also expanded, so that the depth of the hole is also reduced.

The substance handled by the chip of the present invention can be, for example a biological material and the biological material is not particularly limited. However, examples thereof include a cell such as a lymphocyte, an epidermic cell, a hepatocyte, a neurocyte and a stem cell, a protein, a chromosome and a DNA. Further, the substance can be that in which these biological materials are fixed on a carrier such as beads particles.

In the chip of the present invention, by changing a part or the whole of the film temperature to swell or contract a part or the whole of the film, the size of the hole of the hole pattern can be changed arbitrarily. Thus, a biological material housed in the hole of the hole pattern can be caused to be in a clathrated state or liberated state in the hole of the hole pattern by changing the film temperature.

The present invention includes a method for clathrating a biological material in the hole of the hole pattern of the chip including: controlling the film temperature of the chip of the present invention to a temperature at which the diameter of the hole of the hole pattern which the chip has becomes a size capable of housing the biological material to house the biological material in the hole of the hole pattern; and controlling the film temperature of the chip to a temperature at which the diameter of the hole which has housed the biological material becomes a size capable of clathrating the biological material. Further, the present invention includes a method for liberating the biological material clathrated in the chip including controlling the film temperature of the chip which has clathrated the biological material by the above method to a temperature at which the diameter of the hole of the hole pattern which the chip has become a size capable of liberating the biological material.

An uncrosslinked temperature-responsive polymer has a lower critical point temperature (LCST) inherent in each chemical structure. At temperatures which are the lower critical point temperature or lower, the molecule surface exhibits hydrophilicity or water solubility and the molecule is dissolved in water. On the contrary, at temperatures which are the critical point temperature or higher, the molecule surface exhibits hydrophobicity and the molecule is separated out in water. The coated film produced by crosslinking the temperature-responsive polymer used in the chip of the present invention has the above LCST corresponding to the chemical structure of the thermoresponsive polymer used for forming the coated film. In a temperature environment which is LCST or higher, the coated film exhibits hydrophobicity, so that the film expels water out of the inside thereof to be brought into a contracted state. On the contrary, in a temperature environment lower than the LCST, the coated film surface exhibits hydrophilicity, so that the film incorporates water into the inside thereof to be brought into a swollen state and the volume of the film is enlarged.

For example, the lower critical point temperature of an N-isopropylacrylamide polymer is about 32° C. and by maintaining the chip of the present invention using a thermoresponsive polymer having an N-isopropylacrylamide structure at around 35° C. that is the LCST or higher, the coated film is contracted and the hole of the hole pattern is expanded. By sowing a biological material smaller than the hole of the hole pattern over the chip, the biological material can easily move into the hole. Also, a biological material incorporated in the hole can be easily removed out of the hole.

On the contrary, when the present chip is maintained at around 20° C. which is lower than the LCST, the coated film is swollen and the hole of the hole pattern is brought into a narrowed state or an entirely closed state. The biological material incorporated in the hole can be directly grasped or can be caused to be hardly removed out of the hole. Further, the biological material can be caused not to move into the hole.

As a means for maintaining the present chip at a temperature which is the LCST or higher, there can be mentioned a method of putting the substrate in a thermostat bath having a temperature which is the LCST or higher and a method of putting the substrate on a plate having a temperature which is the LCST or higher. Further, it is not necessary to cause the whole chip to be maintained at a temperature which is the LCST or higher and it is also possible to cause only a portion of the coated film around a part in which the hole of the hole pattern is desired to be expanded, to be of a temperature which is the LCST or higher by heating the portion locally using an irradiation of an infrared laser or a small heater.

As a means for causing the present chip to be of a temperature lower than the LCST, there can be mentioned a method of putting the substrate in a thermostat bath having a temperature lower than the LCST and a method of putting the substrate on a plate having a temperature lower than the LCST. Further, it is not necessary to cause the whole chip to be of a temperature lower than the LCST and it is also possible to cause only a portion of the coated film around a part in which the hole of the hole pattern is desired to be narrowed, to be cooled locally by contacting the portion with a liquid having a temperature lower than the LCST which is injected from the tip of a pipette or a syringe, or by using a small peltiert device.

EXAMPLES

Hereinafter, the present invention is described more specifically referring to Examples.

Example 1

Synthesis of Temperature-responsive Polymer having Reactive Group Reactable with Crosslinker 0.91 g ($8.0 \times 10^{-3}$ mole) of N-isopropylacrylamide and 0.23 g ($2.0 \times 10^{-3}$ mole) of hydroxyethylacrylate were dissolved in 30 ml of tetrahydrofuran and a nitrogen bubbling was performed for 10 minutes. Next, as a polymerization initiator, 0.04 g of 2,2'-azobis(isobutylonitrile) was added to the resultant solution and the reaction mixture was heating-refluxed at 70° C. in a nitrogen atmosphere to perform a polymerization for 6 hours. After the polymerization, the solution was poured into 300 ml of n-hexane to separate out a polymer which was filtered off and dried to obtain a white polymer. The structure of the obtained polymer was analyzed by various method and was found to be a polymer (1) having a molar fraction of 80% of an N-isopropylacrylamide structure and a molar fraction of 20% of a hydroxyethylacrylate structure. The molecular weight converted into polystyrene of the polymer was measured by a gel permeation chromatography (GPC) in tetrahydrofuran and was found to be a weight average molecular weight of 63,000 and a number average molecular weight of 45,000.

[Chemical Formula 4]

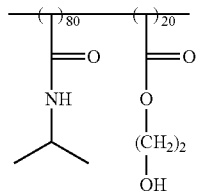

Example 2

Production of Applying Solution of Temperature-Responsive Polymer Having Photosensitivity 100 parts by weight of the above-synthesized temperature-responsive polymer (1), 30 parts by weight of hexamethoxymethylmelamine as a crosslinker and 10 parts by weight of triphenylsulfoniumtriflate as a photoacid generator were dissolved in 250 parts by weight of diacetone alcohol as a solvent and the resultant solution was filtered using a Teflon filter having a pore diameter of 0.40 μm to obtain an applying solution.

Example 3

Formation of Hole Pattern with Temperature-Responsive Polymer (1) . . . Photolithography Method On a glass substrate subjected to a surface treatment with a silane coupling agent having a hydroxyl group at the terminal thereof, the above applying solution was spin-coated at a rotation speed of a spin coater of 3000 rpm. After the coating, the coated substrate was subjected to a heating treatment at 120° C. for 5 minutes to evaporate a solvent to thereby obtain a coated film having a film thickness of 2 μm. Using a mask aligner having a light source of a high-pressure mercury lamp, an exposure to the coated film was performed through a mask. After the exposure, the coated substrate was subjected to a heating treatment at 120° C. for 5 minutes to progress a crosslinking reaction by an acid catalyst reaction only at a portion of the film in which an acid was generated by the exposure. Thereafter, using water of 15° C., a developing treatment for dissolving and removing an uncrosslinked portion was performed for 2 minutes. Subsequently, by elevating the temperature of the developing liquid to 35° C. which is the lower critical temperature or higher to expel water out of the coated film, the film was contracted and with that state, the developing was finished. Thereafter, the substrate was heated and dried at 120° C. for 30 minutes. As the result, a hole pattern of a temperature-responsive polymer of holes having a diameter of 10 μm and a depth of 2 μm was produced in a density of 250,000 pieces/cm² on the substrate.

Example 4

Formation of Hole Pattern with Temperature-Responsive Polymer (2) . . . Inkjet Method 100 parts by weight of the above-synthesized temperature-responsive polymer (1), 30 parts by weight of hexamethoxymethylmelamine as a crosslinker and 10 parts by weight of triphenylsulfoniumtriflate as a photoacid generator were dissolved in 900 parts by weight of diacetone alcohol as a solvent and the resultant solution was filtered using a Teflon filter having a pore diameter of 0.40 μm to obtain an applying solution. On a glass substrate subjected to a surface treatment with a silane coupling agent having a hydroxyl group at the terminal thereof, the above applying solution was sprayed in a form of a hole pattern using an inkjet printer. After the spraying, the whole of the coated film was exposed by a xenon mercury lamp and was subjected to a heating treatment at 120° C. for 5 minutes. As the result, a sprayed temperature-responsive polymer was tightly fixed by a crosslinking reaction to the substrate and a hole pattern of holes having a diameter of 100 μm and a depth of 0.5 μm could be produced in a density of 2,500 pieces/cm² on the substrate.

Example 5

Formation of Hole Pattern with Temperature-Responsive Polymer (3) . . . Screen Printing Method 100 parts by weight of the above-synthesized temperature-responsive polymer (1), 30 parts by weight of hexamethoxymethylmelamine as a crosslinker and 1 part by weight of triphenylsulfoniumtriflate as a photoacid generator were dissolved in 100 parts by weight of diacetone alcohol as a solvent and the resultant solution was filtered using a Teflon filter having a pore diameter of 0.40 μm to obtain an applying solution.

On a glass substrate subjected to a surface treatment with a silane coupling agent having a hydroxyl group at the terminal thereof, the above applying solution was screen-printed in a hole pattern form through a mask for screen-printing. After the printing, the whole of the coated film was exposed by a xenon mercury lamp and was subjected to a heating treatment at 120° C. for 5 minutes. As the result, a printed temperature-responsive polymer was tightly fixed by a crosslinking reaction to the substrate and a hole pattern of holes having a diameter of 100 μm and a depth of 2 μm could be produced in a density of 2,500 pieces/cm² on the substrate.

Evaluation of Temperature Responsivity of Produced Chip

After water was dropped on the chip having the hole pattern produced by the above photolithography method, while maintaining the chip at various temperatures, the variation of the hole size was observed. The result thereof is shown in FIG. 1. When the chip temperature was caused to higher than the LCST (about 35° C.), the temperature-responsive polymer was contracted, and the diameter of the hole of the hole pattern became about 10 μm and the depth became 2 μm. When the chip temperature was caused to lower than the LCST (about 15° C.), the temperature-responsive polymer started to be swollen in both lengthwise and crosswise directions and after about 10 seconds, the diameter of the hole of the hole pattern was contracted to 6 μm and the depth became 6 μm. Further, it has been found that this contracting-swelling behavior can be repeatedly performed according to the change in the chip temperature.

Example 6

Experiment Using Polystyrene Beads

Using a chip having a hole pattern produced by the above photolithography method, a retaining experiment of a minute substance was performed. In the experiment, it was examined that using polystyrene beads having a diameter of 10 μm, each bead was individually fixed and aligned on the chip. The result thereof is shown in FIG. 2. First, in the state in which the chip temperature was maintained at a higher temperature (about 35° C.), a beads-suspension was dropped to the chip and the beads were allowed to be naturally precipitated for 5 minutes. Next, by lowering the chip temperature to a lower temperature (about 15° C.), the temperature-responsive polymer was swollen to grasp tightly only the beads incorporated in the hole. Thereafter, the chip was washed with water of 15° C. in a beaker to wash away excess of beads which were not grasped in the hole. When the chip was maintained at a lower temperature during the washing, the beads in the hole were grasped tightly by the swollen temperature-responsive polymer, so that the beads were not washed away even when washed vigorously. As the result, one bead in each one hole of the hole pattern part can be individually fixed. Further, by returning the chip temperature to a higher temperature (about 35° C.), the temperature-responsive polymer was contracted and could liberate the beads again.

Further, it was attempted to recover only any one bead from the chip by sucking by a capillary. During recovering, by causing the chip temperature to a higher temperature, the diameter of the hole was enlarged and the depth of the hole was decreased, so that the tip of the capillary for recovering beads could be easily approached to the beads and the beads could be reliably recovered.

In this experiment, polystyrene beads having a diameter of 10 μm were used. By varying the size of the hole of the hole pattern, beads or fine particles having any size can be retained, aligned or recovered. Further, a plurality of beads or fine particles to which many types of peptides, sugar chains or oligo-DNA are bonded and which are produced by a combinatorial synthesis can be also retained, aligned or recovered.

Example 7

Retaining Experiment Using Immunocyte

Using a chip having a hole pattern produced by the above photolithography method, a retaining experiment of a fine biological material was performed. In this experiment, it was examined that using lymphocytes (B cell having a diameter of about 6 μm) delivered from a mouse, each lymphocyte was individually retained on the chip. First, in the state in which the chip temperature was maintained at a higher temperature (about 35° C.), a lymphocytes-suspension was dropped to the chip and the lymphocytes were allowed to be naturally precipitated for 5 minutes. Next, by lowering the chip temperature to a lower temperature (about 15° C.), the temperature-responsive polymer was swollen to grasp tightly only the lymphocytes incorporated in the hole. Thereafter, the chip was washed with a PBS buffer of 15° C. in a beaker to wash away excess of lymphocytes which were not grasped in the hole. As the result, one lymphocyte in each one hole of the hole pattern part can be individually fixed. At this time, the cell retained rate was about 16%. Here, the cell retained rate is expressed as "the number of cells retained in the hole on the chip/the number of the holes on the chip×100". Further, by returning the chip temperature to a higher temperature (about 35° C.), the temperature-responsive polymer was contracted and could liberate the lymphocytes again. The result thereof is shown in FIG. 3.

Further, it was attempted to recover only any one lymphocyte from the chip by sucking by a capillary. During recovering, by causing the chip temperature to a higher temperature, the diameter of the hole was enlarged and the depth of the hole was decreased, so that the tip of the capillary for recovering lymphocytes could be easily approached to the lymphocytes and the lymphocytes could be reliably recovered.

In this experiment, as the biological materials, lymphocyte was used. By varying the size and form of the hole of the hole pattern, other biological materials such as blood cells, coliform bacilii, chromosome could be retained, aligned or recovered. Further, a biological material fluorescent-strained or magnetic-labeled could be also retained, aligned or recovered.

Example 8

Controlling Experiment of Transition Temperature

The transition temperature (a temperature at which a temperature-responsive polymer fixed on the chip is changed from a swollen state to a contracted state, or from a contracted state to a swollen state) of a chip having a hole pattern produced by the above photolithography method was specifically examined by observing a condition of swelling-contraction using a microscope, while varying the chip temperature. As the result, the transition temperature of the chip produced by using a temperature-responsive polymer (1) was found to be about 28° C.

On the contrary, the transition temperature of a chip produced using a temperature-responsive polymer synthesized using N-isopropylmethacrylamide instead of N-isopropylacrylamide (As the synthesizing method, the same synthesizing method was repeated except that N-isopropylacrylamide of the temperature-responsive polymer (1) was changed to N-isopropylmethacrylamide) was found to be about 39° C.

Further, the transition temperature of a chip produced using a temperature-responsive polymer synthesized using N-n-propylacrylamide instead of N-isopropylacrylamide (As the synthesizing method, the same synthesizing method was repeated except that N-isopropylacrylamide of the temperature-responsive polymer (1) was changed to N-n-propylacrylamide) was found to be about 16° C.

By changing the type of the temperature-responsive polymer, a chip having a desired transition temperature can be obtained. However, in the case where a biological material such as the cell and protein was handled, for preventing the death or degeneration, it was preferred that the transition temperature is present in a range of higher than 0° C. and lower than 45° C.

Example 9

Experiment for Controlling Depth of Hole of Hole Pattern

Since the depth of the hole of the hole pattern formed by the above photolithography method corresponds to the film thickness of the temperature-responsive polymer during spin-coating, only by controlling the film thickness during the coated film formation, the depth of the hole can be easily controlled. The film thickness of the coated film obtained by changing the polymer concentration in a coating solution and by causing the rotation speed of a spin-coater to 3000 rpm is shown in FIG. 4. Also, the film thickness of the coated film obtained by causing the polymer concentration in an applying solution to 33% by weight and by changing the rotation speed of the spin-coater, is shown in FIG. 5.

Example 10

Experiment for Controlling Volume Increasing Amount by Film Thickness

By the depth of the hole of the hole pattern (corresponding to the film thickness of a temperature-responsive polymer) formed by the above photolithography method, the volume changed amount during the swelling can be controlled, by which the diameter or depth of the hole of the hole pattern during the swelling can be controlled. The more the film thickness of a temperature-responsive polymer is, the more the volume increasing amount is. On the contrary, the less the film thickness of a temperature-responsive polymer is, the less the volume increasing amount is. When a hole pattern of a temperature-responsive polymer having a hole of 10 μm diameter and 2 μm depth (film thickness) and having a pitch of 20 μM was prepared, during the swelling, the hole of the hole pattern was contracted to a diameter of 6 μm and a depth (film thickness) of 6 μm due to the volume increasing of the temperature-responsive polymer. On the contrary, when a hole pattern of a temperature-responsive polymer having a hole of 10 μm diameter and 5.5 μm depth (film thickness) and having a pitch of 20 μm was prepared, during the swelling, the film thickness became 16 μm due to the great volume increasing of the temperature-responsive polymer and further, the hole of the hole pattern could be completely closed.

Example 11

Experiment for Improving Cell Retaining Rate by Controlling Depth of Hole of Hole Pattern In an experiment for retaining an immunocyte using a chip having a hole pattern of a temperature-responsive polymer of holes having a diameter of 10 μm and a depth (film thickness) of 2 μm prepared by the above photolithography method, the cell retaining rate was about 16%. A biological material such as a cell and a chromosome is flexible and is likely to be deformed in comparison with a polystyrene beads or metal fine particles. Therefore, when the hole of the hole pattern has a small depth, there is such a probability that the cell is slightly deformed and escapes out of the hole, during a process for grasping a cell or a washing process. Thus improving the cell retaining rate by changing the depth of the hole (changing the film thickness of a temperature-responsive polymer) was attempted.

A chip having a hole pattern of a temperature-responsive polymer of holes having a diameter of 10 μm and a depth (film thickness) of 3.5 μm changed from 2 μm was prepared by the above photolithography method. The change of the hole depth (film thickness) was performed by changing the polymer concentration in an applying solution during the formation of a spin coated-film from 28% by weight to 33% by weight.

Next, it was examined that using lymphocytes (B cell having a diameter of about 6 μm) delivered from a mouse, each one of lymphocytes was individually retained in the chip. First, in a state where the chip temperature was maintained at a higher temperature (about 35° C.), a lymphocyte suspension was dropped and the lymphocyte was allowed to be naturally precipitated for 5 minutes. Next, by lowering the chip temperature to a lower temperature (about 15° C.), NIPAAm was swollen and only lymphocyte incorporated in the hole was grasped. At this time, a chip of a hole pattern of a hole having 3.5 μm depth (film thickness) has a larger thickness of a temperature-responsive polymer than that of a chip of a hole pattern of a hole having 2 μm depth, so that a larger volume increase could be obtained, an immunocyte was completely enclosed in a swollen temperature-responsive polymer and further, the hole was brought into a completely closed state (FIG. 6).

Further, since all of the temperature-responsive polymer (1), the crosslinker (hexamethoxymethylmelamine) and the acid generator (triphenylsulfoniumtriflate) used in the present experiment are transparent/nonfluorescent relative to a light having a wavelength of 400 nm to 600 nm, even cells embedded in the temperature-responsive polymer could be easily observed with an optical microscope and be easily fluorescent-imaged by adjusting the focus on the embedded cells.

Example 12

Thereafter, the chip was washed with the PBS buffer having a temperature of 15° C. in a beaker to wash away excessive lymphocytes which were not enclosed in the temperature-responsive polymer. The enclosed cells were tightly retained in the hole even by a vigorous washing in the flask. As the result, it could be ensured that each one lymphocyte was individually retained in each one hole of the hole pattern part (FIG. 7). At this time, the cell retaining rate was enhanced to about 87%. Further, the temperature-responsive polymer in a swollen state was a gel and was sufficiently soft, so that the temperature-responsive polymer did not crush the enclosed cells.

Further, when the chip temperature was returned to a higher temperature (about 35° C.), the temperature-responsive polymer was contracted and could liberate the lymphocytes again. Further, it was attempted to recover only any one lymphocyte from the chip by sucking by a capillary. During recovering, by causing the chip temperature to a higher temperature, the diameter of the hole was enlarged again and the depth of the hole was decreased, so that the tip of the capillary for recovering lymphocytes could be easily approached to the lymphocytes and the lymphocytes could be reliably recovered.

Next, a chip having a hole pattern of a temperature-responsive polymer in which the diameter and the depth (film thickness) of the hole were changed respectively to 10 μm and 10 μm, was prepared by the above photolithography method. In the experiment for retaining the immunocyte, two lymphocytes have moved into one hole, so that each one lymphocyte individually could not be retained in each one hole of the hole pattern.

For retaining each one immunocyte (B lymphocyte) having a diameter of 6 individually in each one hole of the hole pattern, the depth of the hole was preferably 1.5 μm or more and 9 μm or less. Further, for obtaining a high cell retaining rate, the depth was more preferably 3 μm or more and 9 μm or less.

Example 13

Examination of Cell Retaining by Controlling Diameter of Hole of Hole Pattern

A chip having a hole pattern of a temperature-responsive polymer of holes having a diameter of 5 μm and a depth (film thickness) of 3.5 μm, was prepared by the above photolithography method. The changing of the diameter of the hole was performed by changing a mask pattern used in a photolithography process. In the experiment for retaining the immunocyte, the diameter of the hole was too small for the lymphocyte to move thereinto, so that each one lymphocyte individually could not be retained in each one hole of the hole pattern part.

A chip having a hole pattern of a temperature-responsive polymer of holes having a diameter of 15 μm and a depth (film thickness) of 3.5 μm, was prepared by the above photolithography method. The changing of the diameter of the hole was performed by changing a mask pattern used in a photolithography process. In the experiment for retaining the immunocyte, three lymphocytes have entered into one hole, so that each one lymphocyte individually could not be retained in each one hole of the hole pattern part.

For retaining each one immunocyte (B lymphocyte) having a diameter of 6 μm individually in each one hole of the hole pattern part, the diameter of the hole was preferably 6 μm or more and 12 μm or less.

Examination of Retaining any Plurality of Cells

By controlling the size, form and depth of the hole of the hole pattern of the temperature-responsive polymer, any number of immunocytes or beads can be retained in one hole. The changing of the size and form of the hole is performed by changing the mask pattern used in the photolithography process and the changing of the hole depth (film thickness) can be easily performed by changing the spin-coating condition.

A chip in which the form of the hole of the hole pattern of the temperature-responsive polymer was caused to be a cuboid having a rectangle (long side 15 μm×short side 8 μm) and having a depth (film thickness) of 3.5 μm, was prepared by the above photolithography method. In the experiment for retaining immunocytes, it could be ensured that two lymphocytes can be retained in one hole (FIG. 8).

By enclosing any number of immunocytes in one hole, the analysis of interactions between a plurality of cells, a cell fusion between a plurality of cells, and the like could be effectively, selectively and easily performed while monitoring at any position on the substrate.

Example 14

Examination with Respect to Lid of Hole Structure

A hole pattern of a temperature-responsive polymer of holes having a diameter of 10 μm and a depth (film thickness) of 3 μm, was prepared on a silicon wafer by the above photolithography method. Next, using DeepRIE, a silicon part exposed to the outside through holes of a hole pattern of a temperature-responsive polymer was dry-etched in an amount of 7 μm in the perpendicular direction. At this time, the temperature-responsive polymer itself was ground down in an amount of 1 μm in the perpendicular direction by dry etching process to reduce the film thickness to 2 μm. This process is shown in FIG. 9.

Using a chip having a temperature-responsive polymer prepared by the above process as a lid of hole structure, the retaining experiment of cells was performed. First, the chip temperature was maintained at a higher temperature (about 35° C.), in a state in which the lid of a temperature-responsive polymer was opened, a lymphocyte suspension was dropped to the chip and the lymphocytes were allowed to be naturally precipitated for 5 minutes. Next, by lowering the chip temperature to a lower temperature (about 15° C.), the temperature-responsive polymer was swollen and it was brought into a state in which the lid of the temperature-responsive polymer was closed. Thereafter, the chip was washed with the PBS buffer having a temperature of 15° C. in a beaker to wash away excessive lymphocytes which were not enclosed in the hole. As the result, each one lymphocyte could be retained individually in each one hole of the hole pattern. At this time, the cell retaining rate was about 85%. Further, when the chip temperature was returned to a higher temperature (about 35° C.), the lid of the temperature-responsive polymer was caused to be opened, so that the lymphocytes could be sucked and recovered by a capillary.

Example 15

Production of Applying Aqueous Solution of Temperature-Responsive Polymer Having Photosensitivity (without Using Organic Solvent)

100 parts by weight of the above-synthesized temperature-responsive polymer (1), 10 parts by weight of hexamethoxymethylmelamine as a crosslinker and 1 part by weight of trimethylsulfoniumtriflate as a photoacid generator were dissolved in 250 parts by weight of water of 15° C. as a solvent and the resultant solution was filtered using a filter having a pore diameter of 0.40 μm to obtain an applying solution.

On a polymethylmethacrylate substrate subjected to a surface treatment with an oxygen plasma, the above applying solution was spin-coated at a rotation speed of a spin coater of 500 rpm. After the coating, the coated substrate was subjected to a heating treatment at 90° C. for 30 minutes to evaporate a solvent to thereby obtain a coated film. Using a mask aligner having a light source of a high-pressure mercury lamp, an exposure to the coated film was performed through a mask. After the crosslinking reaction by the heating after the exposure, using water of 15° C., a developing treatment for dissolving and removing an uncrosslinked portion was performed for 1 minute. As the result, a hole pattern of a temperature-responsive polymer of holes having a diameter of 10 μm was produced in a density of 250,000 pieces/cm² on the substrate. Since water was used as a coating solvent, during the spin-coating, the polymethylmethacrylate substrate as a plastic material was not corroded by the solvent. Further, during the developing by water, since all constituting members were water-soluble, the developing could be advantageously performed without any residue.

Example 16

Production of Chip Using Temperature-Responsive Polymer Derived from Living Body 100 parts by weight of soluble elastin which is a temperature-responsive polymer derived from a living body (derived from bovine) and 10 parts by weight of 4,4'-diazostilben-2, 2'disulfonic acid sodium salt which is a water-soluble bisazide compound as a photocrosslinker were dissolved in 1000 parts by weight of distilled water as a solvent and the resultant solution was filtered using a filter having a pore diameter of 0.40 μm to obtain an applying solution.

On a glass substrate subjected to a surface treatment with a silane coupling agent having a hydroxyl group at the terminal thereof, the above applying solution was spin-coated at a rotation speed of a spin coater of 500 rpm. After the coating, the coated substrate was subjected to a heating treatment at 80° C. for 10 minutes to evaporate a solvent to thereby obtain a coated film. Using a mask aligner having a light source of a high-pressure mercury lamp, an exposure to the coated film was performed through a mask. After the crosslinking reaction by the exposure, using water of 15° C., a developing treatment for dissolving and removing an uncrosslinked portion was performed for 2 minutes. As the result, a hole pattern of a temperature-responsive polymer derived from a living body of holes having a diameter of 10 μm was produced in a density of 250,000 pieces/cm² on the substrate.

After water was dropped on a chip having the hole pattern produced by the above photolithography method, while maintaining the chip at various temperatures, the variation of the hole size was observed. When the chip temperature was caused to be 38° C., the temperature-responsive polymer was contracted and the diameter of the hole of the hole pattern became about 10 μm. When the chip temperature was caused to 15° C., the temperature-responsive polymer started to be swollen and after about 10 seconds, the diameter of the hole of the hole pattern was contracted to 8 μm. Further, it has been found that this contracting-swelling behavior can be repeatedly performed according to the change in the chip temperature.

INDUSTRIAL APPLICABILITY

The chip according to the present invention is useful for various technical fields in which a biological material is necessary to be temporarily fixed, for example for a method of forming an antibody by selecting a specific antigen-specific lymphocyte among various lymphocytes.

Figure 1:
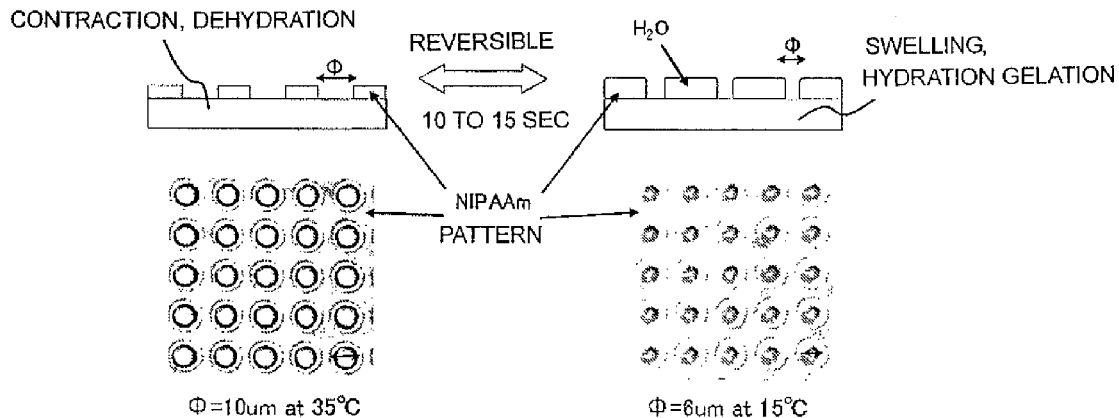
FIG. 1 shows the result of observing the change of the hole size while maintaining the chip at various temperatures, after water was dropped onto the chip having a hole pattern formed by the photolithography method in Example 5.
Figure 2:
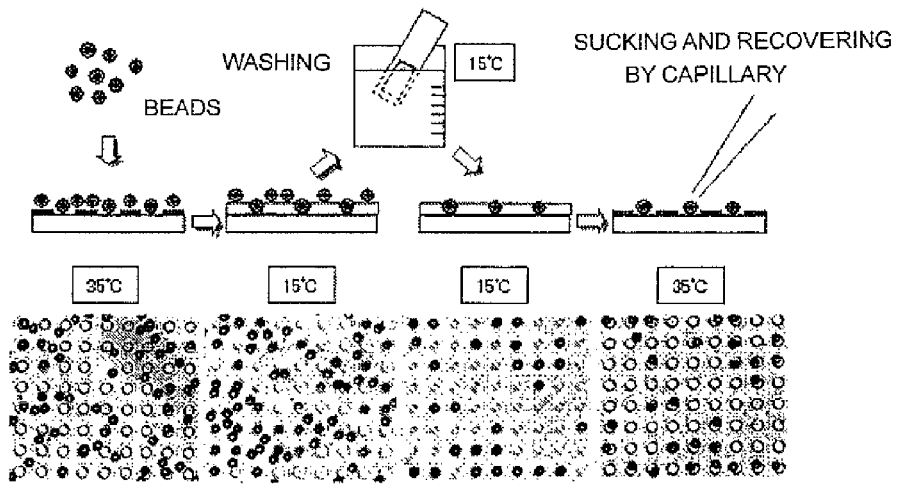
FIG. 2 shows the result of performing the retaining experiment of polystyrene beads having a diameter of 10 μm using a chip having a hole pattern formed by the photolithography method in Example 6.
Figure 3:
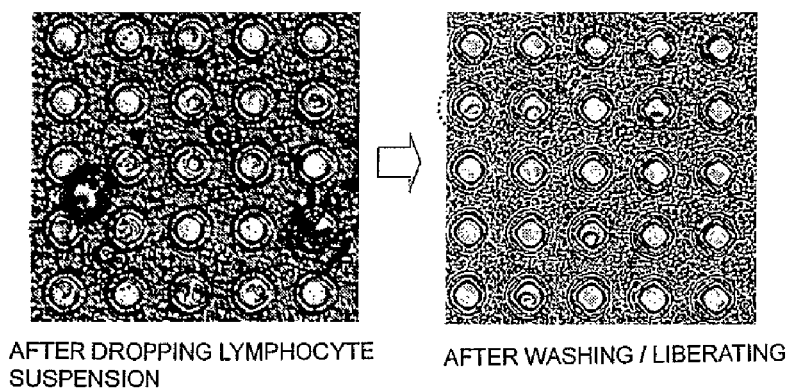
FIG. 3 shows the result of performing the retaining experiment of lymphocytes (B cell having a diameter of 6 μm) using a chip having a hole pattern formed by the photolithography method in Example 7.
Figure 4:
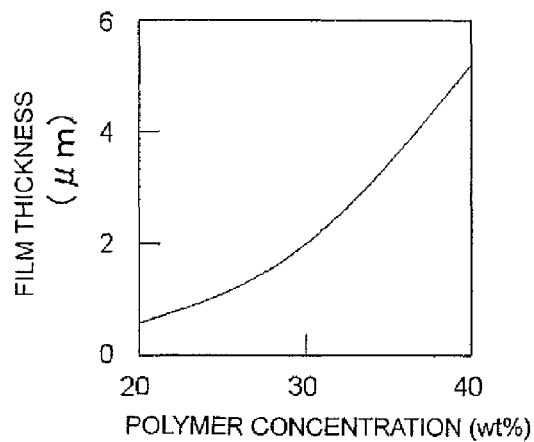
FIG. 4 shows the thickness of the coated film obtained when the polymer concentration in the coating solution is varied and the rotating speed of the spin coater is fixed at 3000 rpm in Example 9.
Figure 5:
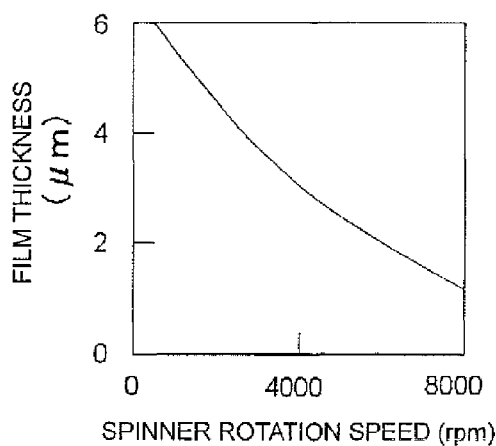
FIG. 5 shows the thickness of the coated film obtained when the polymer concentration in the coating solution is fixed at 33% by weight and the rotating speed of the spin coater is varied in Example 9.
Figure 6:
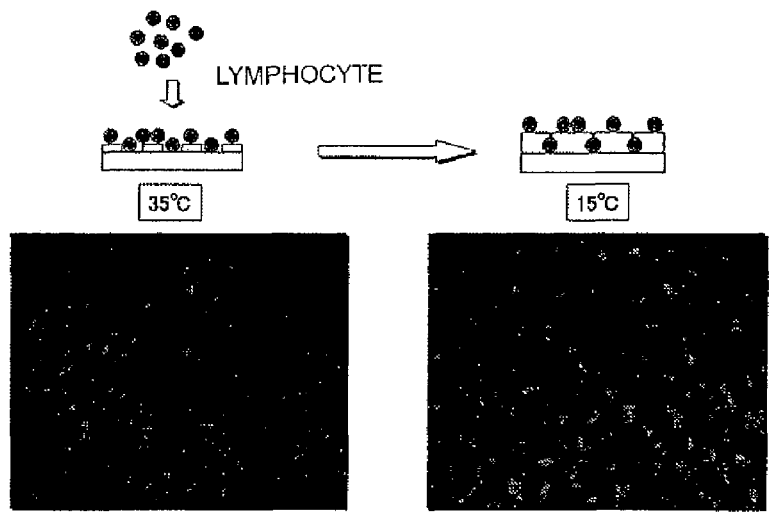
FIG. 6 shows the result of the retaining experiment of lymphocytes in Example 11.
Figure 7:
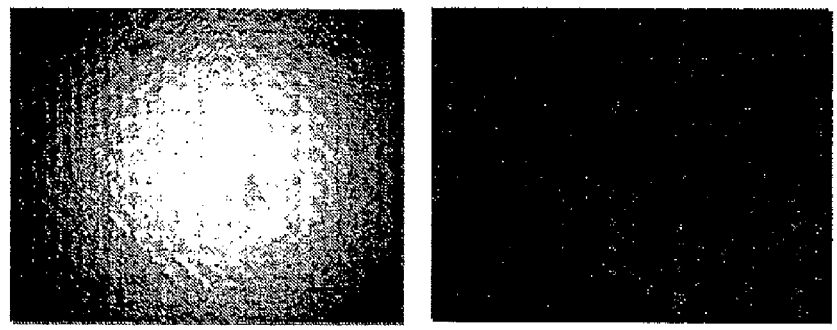
FIG. 7 shows the result of the retaining experiment of lymphocytes in Example 12.
Figure 8:
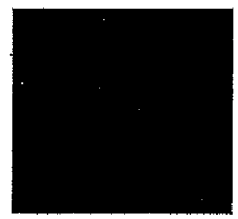
FIG. 8 shows the result of the retaining experiment of lymphocytes in Example 13.
Figure 9:
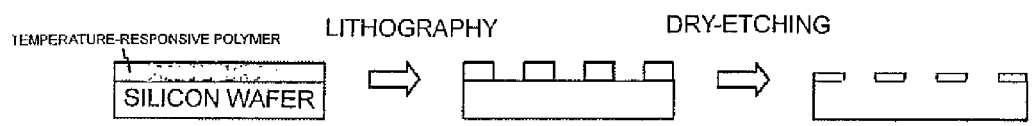
FIG. 9 is a schematic illustration of the process in Example 14.
Figure 10:
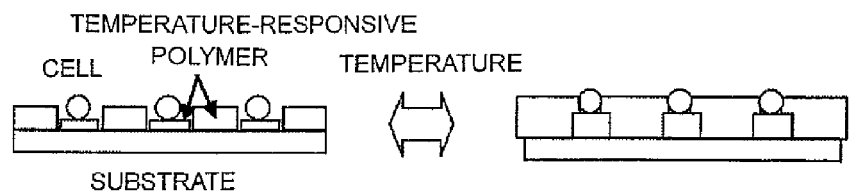
FIG. 10 is a schematic illustration of one aspect of the chip of the present invention.
Figure 11:
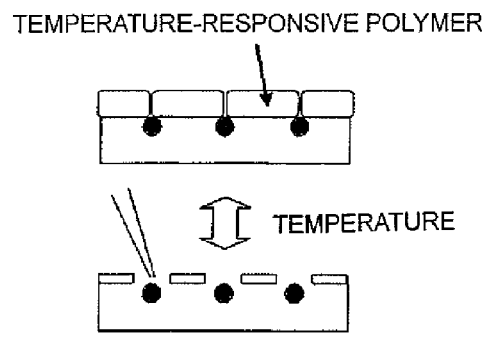
FIG. 11 is a schematic illustration of one aspect of the chip of the present invention.
Figure 12:
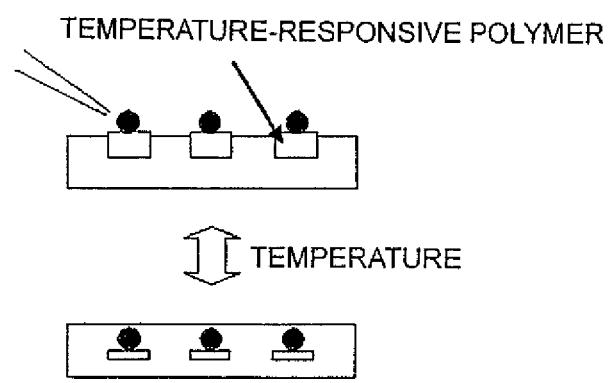
FIG. 12 is a schematic illustration of one aspect of the chip of the present invention.

The invention claimed is:

1. A method for clathrating a biological material in a hole pattern of a film formed on a substrate, the film and substrate forming a chip, the method comprising:
controlling film temperature of the chip to a temperature at which a diameter of a hole of the hole pattern becomes a size capable of housing the biological material;
housing the biological material in the hole of the hole pattern; and
controlling the film temperature of the chip to a temperature at which the diameter of the hole having housed the biological material clathrates the biological material, wherein:
the film comprises a crosslinked product of a temperature-responsive N-alkyl (meth)acrylamide copolymer and a crosslinker,
the N-alkyl (meth)acrylamide copolymer having a weight average molecular weight of 500 to 5,000,000 and a recurring unit represented by general formula (1):

[Chemical Formula 1]

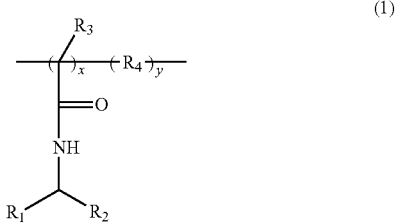

(1)

wherein $R_1$ and $R_2$ may be the same as or different from each other and represent a hydrogen atom or an (1-4C) alkyl group;
$R_3$ represents a hydrogen atom or a methyl group;
$R_4$ represents a hydrocarbon structure having a functional group crosslinkable with the crosslinker; and
x and y are any numbers satisfying numerical formulae: $x+y=1$, $0.6<x\leq0.95$, and $0.05\leq y<0.4$.

2. A method for liberating the biological material clathrated in the chip, the method comprising:
controlling the film temperature of the chip having clathrated the biological material by the method according to claim 1 to a temperature at which the diameter of the hole of the hole pattern of the chip becomes a size capable of liberating the biological material.

3. The method according to claim 1, wherein the film having the hole pattern has a thickness ranging from 10 nm to 100 μm.

4. The method according to claim 1, wherein a hole of the hole pattern has such a size that an inscribed circle thereof has a diameter ranging from 10 nm to 1000 μm.

5. The method according to claim 1, wherein a hole of the hole pattern has a depth ranging from 10 nm to 100 μm.

6. The method according to claim 1, wherein holes of the hole pattern are provided in a density of 1 to 1,000,000,000 holes/cm².

7. The method according to claim 1, wherein the substrate has concave portions below at least some holes of the hole pattern.

8. The method according to claim 1, wherein the crosslinker is a transparent and nonluminescent crosslinker relative to light having a wavelength of 400 nm to 600 nm.

9. The method according to claim 1, wherein the crosslinker is selected from the group consisting of an epoxy-based crosslinker, a melamine-based crosslinker, a glycouril-based crosslinker, and a compound having two or more hydroxyl groups, carboxyl groups, azide groups, or vinylether groups.

10. The method according to claim 1, wherein the crosslinker is a melamine-based crosslinker.

11. The method according to claim 10, wherein the melamine-based crosslinker is selected from the group consisting of hexamethoxymethylmelamine, hexaethoxymethylmelamine, and hexapropoxymethylmelamine.

12. The method according to claim 10, wherein the melamine-based crosslinker is hexamethoxymethylmelamine.

13. The method according to claim 12, wherein the hexamethoxymethylmelamine is transparent and nonluminescent relative to light having a wavelength of 400 nm to 600 nm.

14. The method according to claim 1, further comprising:
temporarily clathrating the biological material in the hole;
controlling the film temperature such that the biological material can be completely released from the film; and
recovering the biological material from the film, wherein the biological material is a cell.

15. The method according to claim 14, wherein the cell is selected from the group consisting of a lymphocyte, an epidermic cell, a hepatocyte, a neurocyte, and a stem cell.

* * * * *